United States Patent [19]
Cincotta et al.

[11] Patent Number: 6,071,914
[45] Date of Patent: Jun. 6, 2000

[54] METHOD FOR INHIBITING NEOPLASTIC DISEASE IN MAMMALS

[75] Inventors: Anthony H. Cincotta, Andover, Mass.; Albert H. Meier, Baton Rouge, La.

[73] Assignees: The Board of Supervisors of Louisiana State University and Agricultural and Mechanical College, Baton Rouge, La.; Ergo Research Corporation, Wakefield, R.I.

[21] Appl. No.: 08/656,103

[22] Filed: May 31, 1996

Related U.S. Application Data

[62] Division of application No. 08/475,296, Jun. 7, 1995.

[51] Int. Cl.[7] .................................................. A61K 31/495
[52] U.S. Cl. .......................... 514/250; 514/288; 514/415; 514/565; 514/567; 514/654; 514/538; 514/908
[58] Field of Search ..................................... 514/250, 288, 514/538, 654, 908, 415, 565, 567

[56] References Cited

U.S. PATENT DOCUMENTS

| | | | |
|---|---|---|---|
| 3,752,814 | 8/1973 | Fluckiger et al. | 544/346 |
| 3,752,888 | 8/1973 | Fluckiger et al. | 514/250 |
| 5,344,832 | 9/1994 | Cincotta et al. | 514/288 |
| 5,468,755 | 11/1995 | Cincotta et al. | 514/288 |
| 5,496,803 | 3/1996 | Meier et al. | 514/12 |
| 5,554,623 | 9/1996 | Cincotta et al. | 514/288 |
| 5,585,347 | 12/1996 | Meier et al. | 514/12 |

FOREIGN PATENT DOCUMENTS

| | | |
|---|---|---|
| 3216869 A1 | 11/1983 | Germany . |
| 3216870 A1 | 11/1983 | Germany . |

OTHER PUBLICATIONS

F. Wauldhaser et al. (1984) Melatonin in Human Body Fluids: Clinical Significance. In *The Pineal Gland* ed. Russel J. Reiter pp. 345–363.

W. Regelson et al. (1987) Melatonin: A Rediscovered Antitumor Hormone? *Cancer Investigation* 5(4):379–385.

B. Neri et al. (1994) Modulation of Human Lymphoblastoid Interferon Activity by Melatonin in Metastatic Renal Carcinoma. *Cancer* 73:3015–3019.

P. Lissoni et al. (1992) Randomized Study with the Pineal Hormone Melatonin versus Supportive Care Alone in Advanced Nonsmall Cell Lung Cancer Resistant to a First–Line Chemotherapy Containing Cisplatin. *Oncology* 49:336–339.

R. Aldeghi et al. (1994) Low–dose Interleukin–2 Subcutaneous Immunotherapy in Association with the Pineal Hormone Melatonin as a First–Line Therapy in Locally Advanced or Metastatic Hepatocellular Carcinoma. *Eur. J. Cancer* 30A(2):167–170.

P. Lissoni et al. (1994) A Randomized Study with the Pineal Hormone Melatonin versus Supportive Care Alone in Patients with Brain Metastases Due to Solid Neoplasms. *Cancer* 73:699–701.

P. Lissoni et al. (1994) Efficacy of the Concomitant Administration of the Pineal Hormone Melatonin in Cancer Immunotherapy with Low–Dose IL–2 in Patients with Advanced Solid Tumors Who Had Progressed on IL–2 Alone. *Oncology* 51:344–347.

P. Lissoni et al. (1995) Immunoendocrine Therapy with Low–Dose Subcutaneous Interleukin–2 Plus Melatonin of Locally Advanced or Metastatic Endocrine Tumors. *Oncology* 52:163–166.

S. Barni et al. (1995) A Randomized Study of Low–Dose Subcutaneous Interleukin–2 Plus Melatonin versus Supportive Care Alone in Metastatic Colorectal Cancer Patients Progressing under 5–Fluorouracil and Folates. *Oncology* 52:243–245.

P. Lissoni et al. (1995) Modulation of cancer endocrine therapy by melatonin: a phase II study of tamoxifen plus melatonin in metastatic breast cancer patients progressing under tamoxifen alone. *British J. of Cancer* 71(4):854–856.

C. Bartsch et al., *J. Neural Transmission*, 52:269–279 (1981).

J. Redman et al., *Science*, 219:1089–1091 (1983).

C. Bartsch et al., *Ann. NY Acad. Sci.*, 719:502–525, (1994).

A.M. Leone et al., *J. Pineal Res.*, 17:17–19, (1994).

Lissoni, P. et al., (1990), A study of pineal–prolactin interaction: prolactin response to an acute melatonin injection in patients with hyperprolactinemia, Medline Abstract, Identifier No.: 90229655.

Lissoni, P. et al., (1989), Endocrine and immune effects of melatonin therapy in metastatic cancer patients, Medline Abstract, Identifier No.: 89289750.

Kikuchi, Y. et al., (1989), Inhibition of human ovarian cancer cell proliferation in vitro by neuroendocrine hormones, Medline Abstract, Identifier No.: 89079088.

Chatterjee, S. et al., (1989), Effects of melatonin on the growth of MtT/F4 anterior pituitary tumor: evidence for inhibition of tumor growth dependent upon the time of administration, Medline Abstract, Identifier No.: 90095797.

Di Stefano, A. et al., (1994), Inhibitory effect of melatonin on production of IFN gamma or TNF alpha in peripheral blood mononuclear cells of some blood donors, Medline Abstract, Identifier No.: 95239580.

Crespo, D. et al., (1994), Interaction between melatonin and estradiol on morphological and morphometric features of MCF–7 human breast cancer cells, Medline Abstract, Identifier No.: 95106114.

(List continued on next page.)

*Primary Examiner*—Richard L. Raymond
*Attorney, Agent, or Firm*—Darby & Darby

[57] ABSTRACT

This invention relates to a method for inhibiting the growth of neoplasms, in a mammal having a prolactin profile. This method involves comparing the prolactin profile of the afflicted mammal to a standard prolactin profile for healthy mammals of the same species and sex and adjusting the prolactin profile of the afflicted mammal to conform to or approach the standard prolactin profile for a mammal of the same species and sex of the afflicted mammal, thereby inhibiting the neoplastic growth.

33 Claims, 4 Drawing Sheets

OTHER PUBLICATIONS

Cos, S. et al., (1994), Differences between pulsatile or continuous exposure to melatonin on MCF–7 human breast cancer cell proliferation, Medline Abstract, Identifier No.: 95007479.

Maestroni, G. et al., (1994), Colony–stimulating activity and hematopoietic rescue from cancer chemotherapy compounds are induced by melatonin via endogenous interleukin 4, Medline Abstract, Identifier No.: 94340606.

Kane, M. et al., (1994), Serum melatonin levels in melanoma patients after repeated oral administration, Medline Abstract, Identifier No.: 94305357.

Furuya, Y. et al., (1994), 5–Fluorouracil attenuates oncostatic effect of melatonin on estrogen–sensitive human breast cancer cells (MCF7), Medline Abstract, Identifier No.: 94291081.

Lissoni, P. et al., (1993), Subcutaneous therapy with low–dose interleukin–2 plus the neurohormone melatonin in metastatic gastric cancer patients with low performance status, Medline Abstract, Identifier No.: 94225687.

Meier, A.H. et al., (1992) Timed bromocriptine administration reduces body fat stores in obese subjects and hyperglycemia in type II diabetics. Experientia 48:248–253.

METHOD FOR INHIBITING NEOPLASTIC DISEASE IN MAMMALS

This is a division, of application Ser. No. 08/475,296, filed Jun. 7, 1995.

BACKGROUND OF THE INVENTION

FIELD OF THE INVENTION

This invention relates to methods for inhibiting neoplasms and their metastases. More particularly, this invention relates to methods employing the alteration of circadian prolactin rhythms to inhibit or ablate neoplasms and their metastases.

Prolactin and Circadian Rhythms

Research has demonstrated that circadian rhythms play important roles in regulating prolactin activities and vice versa.

Publications such as Meier, A. H., Gen. Comp. Endocrinol. 3(Suppl 1):488–508, 1972; Meier, A. H., Trans. Am. Fish. Soc. 113:422–431, 1984; Meier, A. H. et al., Current Ornithology II (ed Johnston R. E.) 303–343, 1984; Cincotta, A. H. et al., J. Endocrinol. 120:385–391, 1989; Meier, A. H., Amer. Zool. 15:905–916, 1975; Meier, A. H., Hormonal Correlates of Behavior (eds. Eleftherton and Sprott) 469–549, 1975 illustrate how circadian rhythms regulate prolactin activities. The resulting daily variations in responsiveness of various cell types to prolactin have a primary role in regulating numerous physiological processes, including fat storage, lipogenic responsiveness to insulin, migratory behavior, metamorphosis, reproduction, growth, pigeon cropsac development and mammary development (Meier, A. H., Gen. Comp. Endocrinol. 3(Suppl 1):488–508, 1972; Meier, A. H., Amer. Zool. 15:905–916, 1975; Meier, A. H. et al., Science 173:1240–1242, 1971). In regulating one of the foregoing physiological activities, prolactin may be observed to produce a stimulatory or an inhibitory effect on a given activity, or to have no effect on it. These varying effects have recently been shown in animals to be a function of the time of the daily endogenous peak (i.e. acrophase) of the rhythm of plasma prolactin concentration or a function of the time of daily injection of exogenous hormone (or of a substance that increases prolactin levels) or of the relation between endogenous peak and any induced peak. Furthermore, high levels of prolactin restricted to a discrete daily interval have a much greater physiologic (e.g. metabolic) effect in animals than do constant high levels throughout a day (Cincotta, A. H. et al., Horm. Metab. Res. 21:64–68, 1989; Borer, K. T. in The Hamster: Reproduction and Behavior (ed. Siegel, H. I.) 363–408, 1985). Such findings demonstrate the existence of daily response rhythms to prolactin by certain types of cells.

The first demonstration of a daily variation in physiological responsiveness to any hormone was the dramatic variation in fattening responsiveness to prolactin in the white-throated sparrow (Meier, A. H. et al., Gen. Comp. Endocrinol. 8:110–114, 1967). Injections at midday of a 16-hour daily photoperiod stimulated 3-fold increases in body fat levels, whereas injections given early in the photoperiod reduced fat stores by 50%. Such daily variations in fattening responses to prolactin were subsequently demonstrated in numerous species of all the major vertebrate classes (Meier, A. H., Amer. Zool. 15:905–916, 1975; Meier, A. H., Hormonal Correlates of Behavior (eds. Eleftherton and Sprott) 469–549, 1975) indicating the fundamental nature of such a temporal organization. The fattening response rhythm persists under constant light conditions (Meier, A. H. et al., Proc. Soc. Exp. Biol. Med. 137:408–415, 1971) indicating that it, like many other endogenous daily variations, is a circadian rhythm.

Additional studies have demonstrated that circadian rhythms have primary roles in regulating numerous physiologic activities, such as lipid metabolism and body fat stores (Meier, A. H. et al., Current Ornithology II (ed Johnston R. E.) 303–343, 1984; Meier, A. H., Amer. Zool. 15:905–916, 1975; Meier, A. H., Hormonal Correlates of Behavior (eds. Eleftherton and Sprott) 469–549, 1975; Meier, A. H. et al., J. Am. Zool. 16:649–659, 1976); Cincotta et al., Life Sciences 45:2247–2254, 1989; Cincotta et al., Ann. Nutr. Metab. 33:305–14, 1989; and Cincotta et al., Horm. Metabol. Res. 21:64–68, 1989. These experiments showed that an interaction of circadian rhythms of liporegulatory hormones (stimuli) and of circadian responses to these hormones (in target cells) determines amount of lipogenesis and fat storage. Thus, high plasma concentrations of prolactin (which serves as the stimulus) occur during the daily interval of maximal fattening responsiveness to prolactin in fat animals, but occur at other unresponsive times of day in lean animals (Meier, A. H., Amer. Zool. 15:905–916, 1975; Meier, A. H., Hormonal Correlates of Behavior (eds. Eleftherton and Sprott) 469–549, 1975; Speiler, R. E. et al., Nature 271:469–471, 1978). Similarly, plasma insulin (which acts as the stimulus) levels are highest during the daily interval of greatest hepatic lipogenic response to insulin in obese hamsters, but at a different time of day in lean hamsters (deSouza, C. J. et al., Chronobiol. Int. 4:141–151, 1987; Cincotta, A. H. et al., J. Endocr. 103:141–146, 1984). The phase relationships of these stimulus and response rhythms are believed to be expressions of neural circadian centers which in turn can be reset by neurotransmitter agents and hormone injections (including prolactin) to produce either fat or lean animals (Meier, A. H., Trans. Am. Fish. Soc. 113:422–431, 1984; Meier, A. H. et al., Current Ornithology II (ed Johnston R. E.) 303–343, 1984; Cincotta, A. H. et al., J. Endocrinol. 120:385–391, 1989; Emata, A. C. et al., J. Exp. Zool. 233:29–34, 1985; Cincotta, A. H. et al., Chronobiol. Int'l 10:244–258, 1993; Miller, L. J. et al., J. Interdisc. Cycles Res. 14:85–94, 1983). Accordingly, timed prolactin administration or enhancement has been shown to act directly upon tissues (e.g. liver in lipogenesis) undergoing circadian rhythms of responsiveness to the hormone to produce immediate variations in net physiologic effects (Cincotta, A. H. et al., Horm. Metab. Res. 21:64–68, 1989) and also acts indirectly by resetting one of the circadian neuroendocrine oscillations of a multi-oscillatory circadian pacemaker system to establish different phase relations between the multiple circadian (neural, hormonal, and tissue) expressions that control lipid metabolism (Meier, A. H., Trans. Am. Fish. Soc. 113:422–431, 1984; Meier, A. H. et al., Current Ornithology II (ed Johnston R. E.) 303–343, 1984; Cincotta, A. H. et al., J. Endocrinol. 120:385–391, 1989; Emata, A. C. et al., J. Exp. Zool. 233:29–34, 1985; Cincotta, A. H. et al., Chronobiol. Int'l 10:244–258, 1993; Miller, L. J. et al., J. Interdisc. Cycles Res. 14:85–94, 1983).

The present inventors have previously shown that prolactin, or substances that affect circulating prolactin levels, also affect circadian rhythms and in fact can be used to modify such rhythms (so that they more closely resemble the rhythms of lean, healthy, young individuals of the same sex) and to reset such rhythms (so that the modified rhythms persist in the modified condition). See, e.g. U.S. patent applications Ser. No. 08/158,153, now U.S. Pat. No. 5,468,755, 07/995,292, now U.S. Pat. No. 5,585,347, 07/999,685, abandoned, and U.S. Pat. No. 5,344,832. This prior work by the present inventors has been clinically tested in humans afflicted with various physiological disorders (obesity, diabetes, atherosclerosis, hypertension, immune dysfunction, and others) with good results.

In particular, in U.S. patent application Ser. No. 07/995,292, now U.S. Pat. No. 5,585,347 and in its continuation-in-part Ser. No. 08/264,558, now abandoned filed Jun. 23, 1994, the present inventors disclose a method for the reduction in a subject, vertebrate animal or human, of body fat stores, and reduction of at least one of insulin resistance, hyperinsulinemia, and hyperglycemia, and other metabolic diseases, especially those associated with Type II diabetes. More specifically, the foregoing application discloses methods for: (i) assessing the daily prolactin level cycles of a normal (healthy) human or vertebrate animal (free of obesity, disease or other disorder); (ii) diagnosing aberrant daily prolactin level cycles of a human or vertebrate animal; and (iii) determining the appropriate adjustments that need to be made to normalize such aberrant prolactin level cycles. This method involves the administration of at least one of a prolactin reducer and/or a prolactin enhancer at a first predetermined time (or times) within a 24-hour period (if only a prolactin reducer is administered) and/or at a second predetermined time (or times) of a 24-hour period (if a prolactin enhancer is administered). This therapy, when continued for several days, weeks or months, results in the long-term adjustment of aberrant or abnormal prolactin level cycles so that they conform to (or approach) normal prolactin level cycles. In most cases, this benefit persists over the long-term even after cessation of therapy. As a result, aberrant physiological parameters associated with various metabolic disorders are restored to normal levels or are modified to approach normal levels. Although this method is applied to all persons having aberrant prolactin levels during at least a portion of a 24-hour period, importantly, there is neither teaching of the possibility of applying it to persons with neoplastic disease, nor is there teaching of the possibility of applying this method to the treatment of neoplastic conditions.

Corticosterone and Circadian Rhythms

The secretory rates of corticosterone in humans is high in the early morning but low in the late evening. Plasma corticosterone levels range between a high of 0.2 mcg/ml an hour before waking in the morning and a low of about 0.05 mcg/ml around 12 AM. This effect is the result of a 24 hour cyclic alteration in the signals from the hypothalamus that cause corticosterone secretion. When a mammal changes sleep habits, the cycle changes correspondingly. Conversely, when the cycle changes, sleep habits are changed. Thus corticosterone administration can be used to synchronize the circadian rhythms of a number of experimental mammals which have been deprived of a photoperiod by exposure to constant light, as is done in the several of the Examples described below. The secretory pattern of corticosterone is different for each species but can easily be determined by assaying for the hormone at various time intervals during dark and light portions of the photoperiod.

While it was well known in the art that it was possible to control many metabolic disorders by adjustment of prolactin rhythms, it was completely surprising and unexpected to find that if prolactin rhythms in mammals afflicted with neoplasms and metastases were adjusted to conform to or approach the rhythms found in young, healthy, lean individuals of the same species and sex, neoplastic and metastatic growth was inhibited to a very significant extent.

SUMMARY OF THE INVENTION

It has long been known that mammals (including humans) suffering from neoplastic diseases have abnormal prolactin profiles. It has now unexpectedly been discovered that neoplasms and their metastases in mammals (including humans) may be treated by modifying the abnormal prolactin profile of the mammal afflicted with neoplastic disease so that the profile approaches or conforms to the prolactin profile of a lean, young healthy mammal of the same species and sex. The abnormal prolactin profile of the afflicted mammal may be modified by (i) direct administration of prolactin, (ii) adjusting the prolactin profile by timed administration of prolactin modulators, i.e. prolactin enhancers and/or reducers, or by (iii) resetting the circadian rhythm of the afflicted mammal to a normal phase and amplitude through the timed administration of prolactin enhancers (such as melatonin) and prolactin reducers (such as Bromocriptine).

Thus, one aspect of the present invention is a method for treating or inhibiting neoplasms and their metastases in mammals by administration to the mammal of a prolactin reducer and/or enhancer or a timed sequential administration of a prolactin enhancer and reducer at a predetermined time or times during a 24-hour period that results in modification of the mammal's abnormal prolactin profile so that it approaches or conforms to the prolactin profile of a young healthy mammal of the same species and sex.

Another aspect of the present invention is directed to a method for treating or inhibiting neoplasms and their metastases on a long-term basis by continuing the foregoing timed administration(s) of prolactin reducer and/or enhancer until the altered prolactin rhythm of the subject is reset and persists in this reset condition for an extended period of time even after cessation of therapy, resulting in persistence of inhibition of neoplastic growth.

Thus, the present invention is directed to treating or inhibiting the growth of neoplasms in mammals by adjusting the circadian rhythm of prolactin. The method of the invention achieves neoplastic growth inhibition by normalizing the circadian rhythm for prolactin of the subject receiving treatment to resemble that of a healthy young subject.

Advantages of the present invention include:

the ability to combat neoplasms without the debilitative effects of chemotherapeutic agents.

the ability to inhibit the metastatic growth of neoplasms which often accompanies removal of the primary neoplastic mass.

the neoplastic growth inhibiting and treatment benefits of the present invention may persist long-term even after the administration of prolactin modulators has been discontinued.

Other features and advantages of the present invention will be apparent from the following description taken in conjunction with the accompanying drawings.

DETAILED DESCRIPTION OF THE INVENTION

All patents, patent applications, and literature references discussed in this specification are hereby incorporated by reference. In case of a conflict in terminology, the present disclosure including its definitions controls.

"Prolactin reducer" refers to a substance or composition that has the ability to lower circulating prolactin levels upon administration to a mammal; "Prolactin enhancer" refers to a substance or composition that has the ability to raise circulating prolactin levels, and includes prolactin itself.

Prolactin reducers and prolactin enhancers are referred to collectively as "prolactin modulators".

"Prolactin profile" of a subject is a depiction of circulating prolactin levels and their variation over all or part of a 24-hour period, and therefore is expression of all or part of the subject's plasma prolactin daily rhythm.

"Healthy" is a young, lean subject free of disease including malignancies, neoplasms, immune system dysfunctions and metabolic abnormalities. A healthy subject is one with a normal prolactin profile, i.e., a prolactin profile that does not depart from the baseline of that subject's species and sex by more than one standard error of the mean (SEM). The normal or baseline prolactin profile for healthy male and female humans is depicted in FIG. 1.

Figure 1:
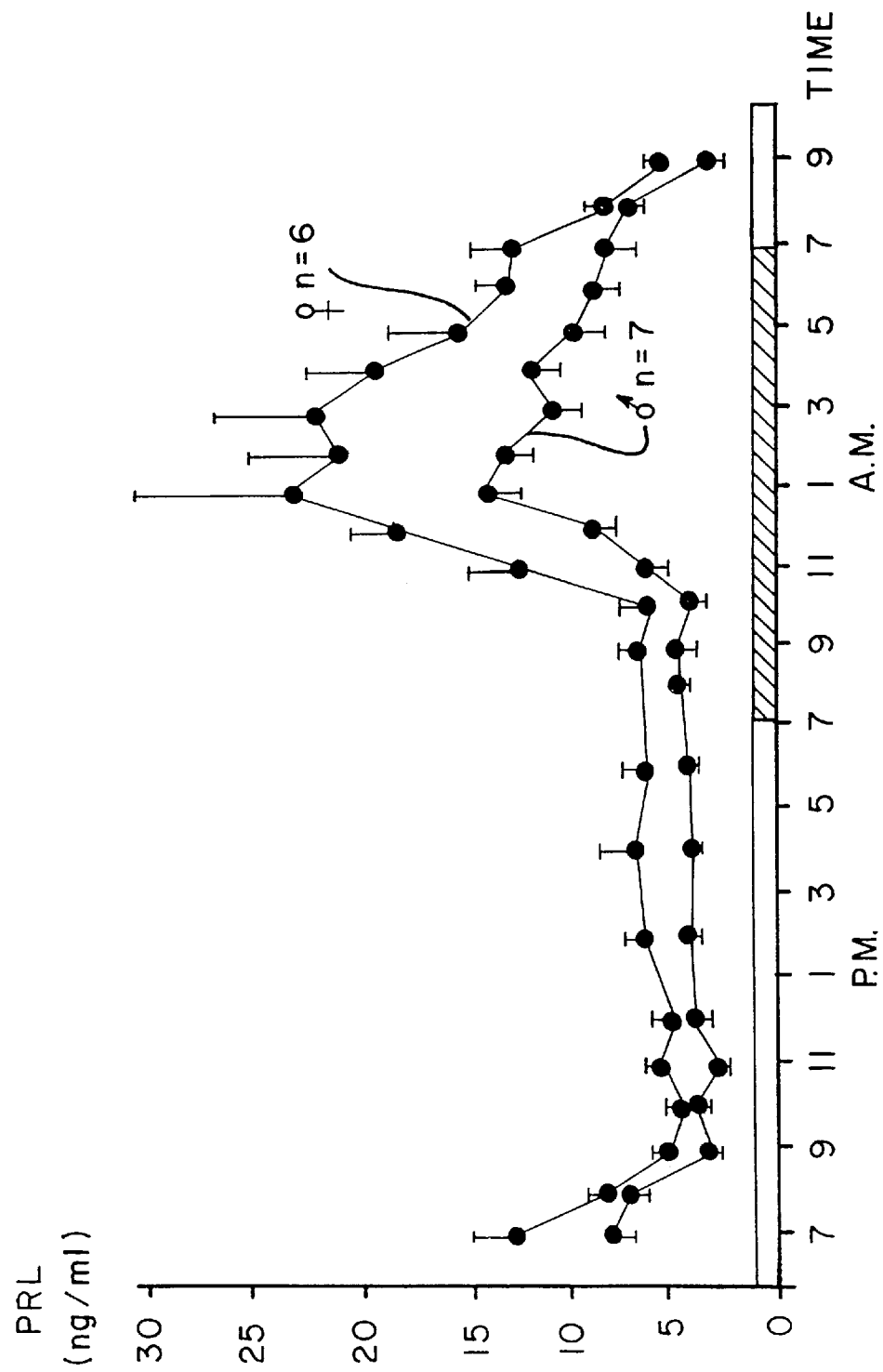
FIG. 1 depicts the normal or baseline prolactin profile for healthy male and female humans.

In order to avoid "false positives" a subject will not generally be considered to have an abnormal prolactin profile unless:

(a) the subject's daytime blood prolactin level is at least 1 SEM higher than the baseline at two (or more) time points during daytime spaced apart by at least one and preferably by at least two hours; or (b) the subject's daytime blood prolactin level is at least 2 SEM higher than the baseline at one time point during daytime; or (c) the subject's night time blood prolactin level is at least 1 SEM below the base line at two (or more) time points spaced apart (as in (a)); or (d) the subject's night time blood prolactin level is at least 2 SEM below the base line at one time point during night time; or The human male and female prolactin baselines are depicted in FIG. 1. One SEM during waking hours (07:00–22:00) is about 1–2 ng/ml for males and about 1–3 ng/ml for females; one SEM during night time (22:00–07:00) is about 3 ng/ml for males and about 3–6 ng/ml for females.

The characteristics of the prolactin level daily rhythm or profile that are to be approached or conformed in humans include achieving low prolactin levels (2–7 ng/ml of plasma) for males and 2–10 ng/ml for females) during most or all of the time period between 07:00 and 22:00 h.

Ideally, a peak prolactin level should also be achieved between the hours of 22:00 and 07:00 (preferably between 1:00 and 4:00) (the peak should be at least 10 ng/ml and most preferably between 10–15 ng/ml for males and at least 15 ng/ml and preferably between 15 and 25 ng/ml for females).

Effects of Prolactin Modulators on Neoplastic Disease

The present invention provides a method for treating and inhibiting the growth of neoplasms and their metastases (e.g. decreasing the amount of neoplastic tissue, or decreasing metastatic burden after primary tumor removal, if the neoplasm is solid) in mammals with a substantial neoplastic tissue burden or with potential metastatic growth following removal of a primary neoplastic tissue mass. This can be accomplished by administration of a prolactin modulator(s) at predetermined times during a 24-hour period. The time for administration of the prolactin modulator is selected so as to adjust the prolactin profile of the mammal receiving treatment to conform or approach the prolactin profile of a healthy mammal of the same sex and species.

It has been found that administration of prolactin enhancers is inhibitory to neoplastic growth in mammals when given at timed intervals during a 24 hour period which correspond to the peak of prolactin secretion in healthy mammals. Timed prolactin injections in neoplasm bearing mice which have had their circadian rhythms synchronized with either a defined photoperiod or with corticosterone injections were shown to exhibit a decreased neoplastic tissue burden as compared with neoplasm bearing mice which did not receive timed prolactin injections. It has also been found that the effect of in vivo prolactin modulation of in vivo neoplastic tissue and metastasis inhibitory responses is time-of-day dependent.

A time-of-day dependent role for prolactin in inhibiting neoplastic disease is also indicated by results of experiments on mice which decrease prolactin blood levels (by administration of a prolactin reducer) during specific daily intervals of lack of neoplastic growth inhibitory response to exogenous prolactin. Time-response studies with bromocriptine, a D2 dopamine agonist which inhibits endogenous prolactin secretion, indicate that bromocriptine increases the inhibition of neoplastic and metastatic growth when it is administered at predetermined times during a 24 hour period to reduce prolactin levels to those found in healthy animals of the same sex and species during such time period. These results are illustrated in Example 5.

Further confirmation of the time-of-day dependent role for prolactin in inhibiting neoplastic growth is illustrated in Example 6. In this experiment the prolactin blood levels of mice are decreased by the administration of bromocriptine, a prolactin reducer, during the specific daily interval of lack of responsiveness of neoplastic growth inhibitory activity to prolactin as is found in Example 5 above and prolactin levels are increased by the administration of melatonin, a prolactin enhancer to determine the specific daily interval of increased responsiveness of neoplastic growth inhibitory activity to prolactin. It is found that the combination of administration of a prolactin enhancer at the time during a 24 hour period when prolactin levels are peaking in healthy mice and administration of prolactin reducer at the time during a 24 hour period when prolactin levels are at their nadir in healthy animals exerts a potent inhibitory effect on growth of neoplasms.

The above results indicate the neoplastic growth inhibitory effects of prolactin levels and the relationship between neoplastic growth inhibition to exogenous prolactin (or prolactin enhancers or reducers) and the time of day of prolactin reduction or enhancement.

Although the foregoing experiments are conducted in mice, they are dependent on features of physiology that are common to mammals having a prolactin daily rhythm including humans. These results show that blood levels of prolactin can be manipulated during predetermined intervals to bring about a desirable result with regard to inhibition of growth of neoplasms and their metastases.

According to the method of the present invention, the alteration of prolactin levels of a subject at particular times of day provides methods for inhibiting neoplastic growth in the subject or inhibiting the growth of metastases in a subject. The method may be used on all types of neoplasms, including but not limited to sarcomas, carcinomas, glioblastomas, melanomas, lymphomas, adenomas, and leukemias.

Use of Prolactin Modulators to Inhibit Neoplasms and Their Metastses Adjustine Prolactin Rhythms of Subjects With Neoplasms and/or Metastases It is known that young adult healthy mammals of a given species (and sex), e.g. humans (suffering from no hormonal or metabolic disorders or cancer or other infection or ailment) have highly predictable daily prolactin level rhythms or profiles. The baseline curve for healthy human males and females in FIG. 1 is derived from such young healthy individuals.

The phase relationship between the daily peaks of the stimulus (plasma prolactin) rhythm and response (neoplastic growth inhibition) to prolactin has been found to be important in neoplastic growth inhibitory activity. Environmental and pharmaceutical factors influencing either of these rhythms can be expected to impact neoplastic growth.

Figure 3:
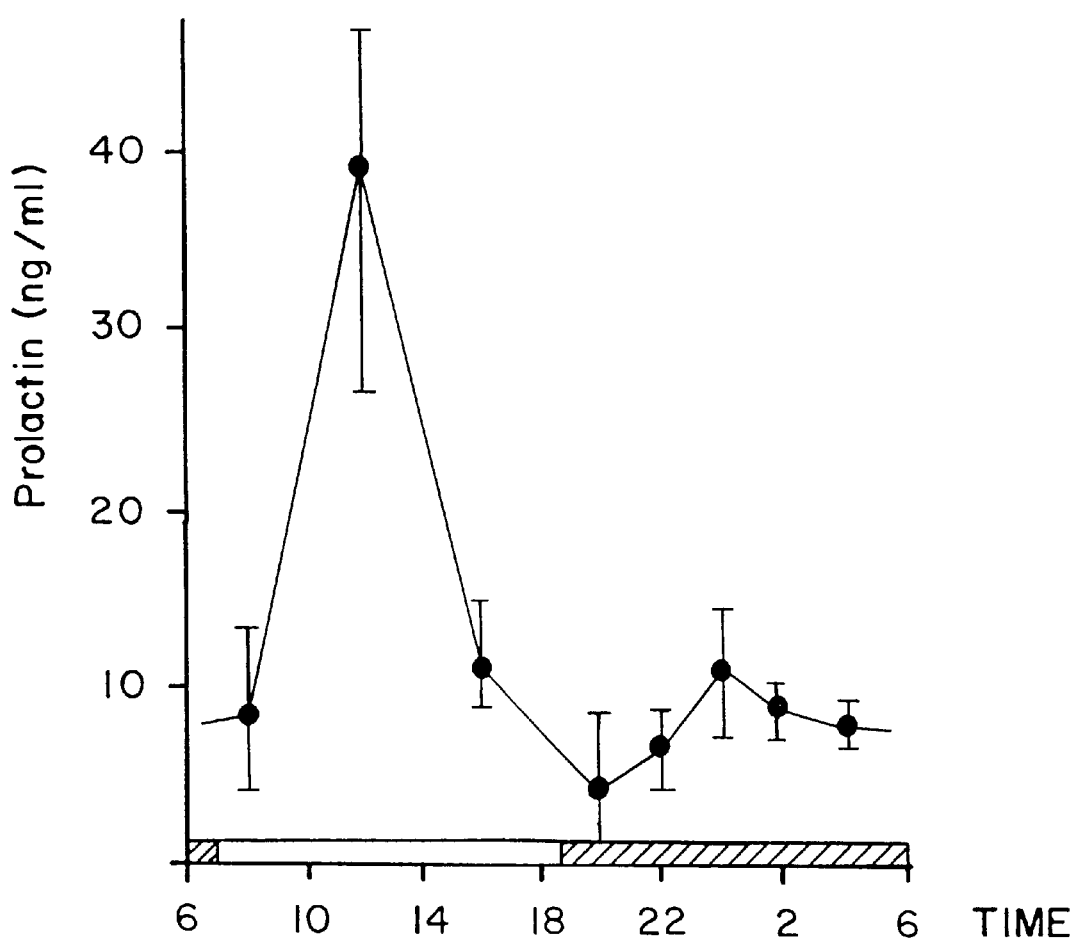
FIG. 3 is the prolactin daily rhythm or profile curve for breast cancer patients with tumors.

Humans with a neoplastic disease, such as breast cancer, have pertrbed prolactin rhythms, which is apparent in a comparison of the prolactin rhythms of healthy women with the rhythms of women with breast cancer, which rhythms are shown in FIGS. 1 and 3, respectively. Humans with neoplastic disease thus can benefit to a significant extent by adjustment of their prolactin daily rhythms (as expressed by their prolactin profile) to conform to or approach the normal or baseline prolactin curve of FIG. 1. An adjusted prolactin profile approaches a normal or healthy profile, if all or a portion of the abnormal profile moves in the correct direction by at least 2 ng/ml.

Before this adjustment can be accomplished:
(i) the prolactin levels of the neoplasm bearing human should be ascertained by assaying blood samples of the neoplasm bearing human at certain spaced apart intervals within a 24 hour period (or portions thereof), and
(ii) the resultant prolactin profile of the neoplasm bring human should be compared to the prolactin profile for a healthy human of the same sex.

Depending on the difference between (i) and (ii), the adjustment then involves administering one or both of the following:
(a) a prolactin reducer at a first predetermined time (or at more than one first predetermined time) and in a first amount effective to reduce day time prolactin levels if these levels are too high; and
(b) a prolactin etaancer at a second predetermined time (or at a plurality of second predetermined times) and in a second amount effective to increase night time prolactin levels if these levels are too low.

In general, if a prolactin level altering substance is to be administered, appropriate allowance should be made with reeeect to the time of administration to permit that substance (depending on its pharmacolinetic properties) to affect prolactin levels such that prolactin levels would be modified during the appropriate time of day. Thus, the prolactin altering substance will be administered as follows:
(a) if prolactin is administered, it will be administered, preferably by injection, during the time interval that prolactin levels need to be raised;
(b) if a prolactin enhancer other than prolactin is administered, it will be administered during or some time shortly prior to the time interval when prolactin levels need to be raised (how much prior depends on pharmacolinetic properties: 0–3 hours prior has generally been found to be effective); and
(c) if a prolactin reducer is administered it will also be administered during or slightly prior to the time that prolactin levels need to be reduced (again, 0–3 hours prior has generally been found to be effective).

In the method of the present invention, "prolactin enhancer" includes prolactin as well as substances which increase circulating prolactin levels (e.g. by stimulating prolactin secretion). Non-limiting examples of a prolactin enhancer include prolactin; melatonin; dopamine antagonists such as metoclopramide, haloperidol, pimozide, phenothiazine, domperidone, sulpiride and chlorpromazine; serotonin agonists, i.e., MAO-A inhibitors, e.g., synthetic morphine analogs, e.g., methadone; antiemetics, e.g., metoclopramide; estrogens; and various other serotonin agonists, e.g., tryptophan, 5-hydroxytryptophan (5-HTP), fluoxetine, and dexfenfluramine. Moreover, the non-toxic salts of the foregoing prolactin enhancing compounds formed from pharmaceutically acceptable acids are also useful in the practice of this invention. Melatonin and 5-HIP have been found particularly useful in the practice of this invention.

Nonlimiting examples of prolactin reducers include prolactin-inhibiting dopamine agonists (D2 agonists) such as dopamine and certain ergot-related prolactin-inhibiting compounds. Nonlimiting examples of dopamine agonists are 2-bromo-alpha-ergo-criptine;6-methyl-8beta-carbobenzyloxy-aminoethyl-10-alpha-ergoline; 8-acylaminoergolines, are 6-methyl-8-alpha-(N-acyl)amino-9ergoline and6-methyl-8alpha-(N-phenylacetyl)amino-9-ergoline; ergocornine; 9, 10-dihydroergocornine; and D-2-halo-6-alkly-8-substituted ergolines, e.g., D-2-bromo-6-methyl-8-cyanomethylergoline; carbi-dopa and L-dopa; and lisuride. Moreover, the non-toxic salts of the prolactin-reducer compounds formed with pharmaceutically acceptable acids are also useful in the practice of this invention. Bromocriptine, or 2-bromo-alpha-ergocryptine, has been found particularly useful in the practice of this invention.

The modulation of neoplastic growth inhibition induced by prolactin enhancers or reducers is expected to be dose-dependent over a range of dosages.

In treating mammals, generally, dosages of the prolactin reducer and/or enhancer, respectively, are each given, generally once a day, generally over a period ranging from about one month to about one year, but treatment can continue indefinitely (if necessary or desired) for months or even several years. The preferred prolactin reducer (accelerated release bromocriptine) is given at daily dosage levels ranging from about 3 micrograms to about 300 micrograms, preferably from about 10 micrograms to about 100 micrograms, per kg. of body weight, and a preferred prolactin enhancer, melatonin, is given at daily dosage levels ranging from about 10 micrograms to about 800 micrograms, preferably from about 10 micrograms to about 200 micrograms, per kg. of body weight per day to modify, or alter, the prolactin profile. Another preferred prolactin enhancer, 5-hydroxytryptophan, is given at daily dosage levels ranging from 500 micrograms to about 13 milligrams per kg. of body weight, preferably from 1 milligram to 2.5 milligrams per kg. of body weight. The exact dosage within these ranges to be administered to each subject will depend upon the particular prolactin modulator, the subject's age, stage of disease, physical condition and responsiveness to treatment.

In order to adjust the prolactin profile of a mammal, administration of either or both prolactin altering substances can be continued for a time sufficient to reset the circadian plasma prolactin rhythm to the phase and amplitude to that of a healthy subject of the same sex and species at which time treatment may be discontinued. If the subject suffers a relapse, treatment may be resumed in order to adjust the prolactin profile of the subject to conform or approach the prolactin profile of a healthy subject of the same sex and species. The time needed for resetting varies but is generally within the range of one month to one year. For some patients (e.g. patients in particularly poor physical condition, or those of an advanced age) it may not be possible to reset their prolactin rhythm within the above time periods and such patients may require a longer, or even continuous, treatment with prolactin enhancers and/or reducers. The dosage and timing information set forth above is designed for bromocriptine, melatonin, and 5-hydroxytryptophan and will have to be altered for other agents using the dosage and timing methodology disclosed herein.

In the practice of this invention, a prolactin reducing compound, and/or a prolactin enhancer are administered daily to a subject preferably orally, or by subcutaneous, intravenous or intramuscular injection. The reducer or enhancer can also be administered by inhalation. Dermal delivery systems e.g., skin patches, as well as suppositories and other well-known systems for administration of pharmaceutical agents can also be employed. Treatment generally lasts between about one month and about one year on average in humans. The administration of the prolactin reducer and/or prolactin enhancer in this manner will thus reset the phase and amplitude of the neural oscillators that control the body's ability to inhibit neoplastic growth to facilitate inhibition of neoplastic growth on a long term basis (e.g., several months or years). An improvement in the ability to inhibit neoplastic growth can be assessed by observation of partial or total ablation of the neoplasm or metastatic regrowth after the removal of a primary neoplasm. Instead of measuring neoplastic burden directly, well-known assays of tumor burden (e.g. assays of neoplasm-specific antigens, magnetic resonance imaging, CAT scanning, X-rays, ultrasound, counting blood-borne neoplastic cells in blood samples, etc.) can be used to assess the effect of treatment with timed administration of prolactin modulators.

The following more specific guidelines will generally be followed to initially determine prolactin modulator administration timing, for a period of treatment of approximately 26 weeks for human subjects:

(i) Give prolactin reducers from 0600 hours to 1000 hours in a dosage range sufficient to decrease diurnal prolactin levels to within 1 SEM of the normal range of diurnal prolactin levels found in humans without neoplastic disease.

(ii) Give prolactin enhancers before or at bedtime in a dosage range sufficient to increase serum prolactin levels to at least the level of a normal, healthy human without neoplastic disease.

The aspect of the invention directed to an inhibition of neoplastic growth by resetting the prolactin profile of a mammalian subject (animal or human) having an aberrant prolactin profile to conform to or approach the prolactin profiles for young healthy members of the same species and sex (e.g. the baselines of FIG. 1) involves administration of a prolactin reducer, or a prolactin enhancer, or both, at predetermined dosages and times dictated by the aberrant (pre-treatment) prolactin profile of the subject to be treated. The amounts of prolactin reducers and/or enhancers that are required to bring about this modification are within the same ranges as set forth above, but the time(s) of administration of these prolactin modulator(s) is determined by reference to how much and when the aberrant profile differs from the normal prolactin profile (baseline curve). Methods for determining the amounts and timing of administration are also set forth in our copending U.S. patent application Ser. No. 07/995,292 and its C-I-P, Ser. No. 08/264,558 filed Jun. 23, 1994, both incorporated by reference. Another method is to give up to 4.8 mg/day of bromocriptine as follows; 0.8 mg/day for each of the first 7 days; beginning on day 8 and for 7 days thereafter, 1.6 mg/day is administered to the patient; beginning on day 15 and for 7 days thereafter, 2.4 mg/day are administered; beginning on day 22 and for 7 days thereafter, 3.2 mg/day is administered; beginning on day 29 and for 7 days thereafter, 4.0 mg/day is administered and beginning on day 36 and for 7 days thereafter, 4.8 mg per day is administered for 7 consecutive days. A preferred accelerated release bromocriptine dosage form has been disclosed in copending U.S. patent application Ser. No. 08/171,897, now abandoned in favor of continuing application Ser. No. 08/459,021, allowed also incorporated by reference.

The present invention is further described and will be better understood by referring to the working Examples set forth below. These non-limiting Examples are to be considered illustrative only of the principles of the invention. Further, since numerous modifications and changes will readily occur to those skilled in the art, it is not desired to limit the invention to the exact construction and operation shown and described. Accordingly, all suitable modifications and equivalents may be used and will fall within the scope of the invention and the appended claims.

EXAMPLE 1

Plasma Prolactin in Normal and Tumor (EMT-6 Fibrosarcoma) Bearing Mice

Adult (6–7 week old) Balb/C mice (Average weight 20 gms) housed on 12 hour daily photoperiods and allowed to feed ad libitum, were injected subcutaneously in the hindquarter with fibrosarcoma cells (EMT-6) at a dose of $1.7 \times 10^6$ cells. A control group remained uninjected. Fourteen to 21 days later when tumor diameters were 6–9 mm, animals from the injected and uninjected control groups were sacrificed at 0, 4, 8, 12, 16, or 20 hours after light onset (HALO) (n=6–8 per time point per group) and plasma was collected for the analyses of plasma prolactin. Plasma prolactin concentration (FIG. 2) was measured by radioimmunoassay (RIA) utilizing a homologous mouse prolactin RIA kit from Dr. A. F. Parlow, Torrance, Calif. The results of this experiment show that neoplasm bearing mammals have a prolactin profile which is deranged relative to that of a healthy, non-neoplasm bearing mammal of the same species and sex.

EXAMPLE 2

Effect of Timed Prolactin Injection on Tumor Growth (EMT-6 Fibrosarcoma) in Balb/C Mice Adult (6–7 week old) Balb/C mice (Average weight 20 gms) were injected with $1.7 \times 10^6$ EMT-6 cells (fibrosarcoma) in the hind quarter while maintained (from birth) in a 12 hour daily photoperiod. The day following inoculation, animals were divided into two groups (n=10 per group) and injected daily with ovine prolactin (20 μg/mouse) or vehicle (control group) at 10 HALO for 10 days (Exp. 1) or 14 days (Exp. 2) and tumor growth was monitored by measuring tumor size with calipers. The results are shown in Table 1, infra:

TABLE 1

|  |  | CONTROL | PROLACTIN |
|---|---|---|---|
| Experiment 1 | Tumor diameter | 7 ± 0.4 mm$^3$ | 4 ± 0.5 mm$^3$* |
| Experiment 2 | Tumor volume | 1200 ± 390 mm$^3$ | 700 ± 100 mm$^3$* |

*$P < 0.05$ versus control

The results of this experiment show that prolactin administration 10 HALO to tumor bearing mice results in decreasing the size of the resulting tumors. The peak of plasma prolactin in healthy, non-tumor bearing Balb/C mice occurs at 8–12 HALO. Thus, administration of prolactin during the time of peak plasma prolactin in healthy non-tumor bearing mice results in decreased tumor growth.

when they were injected in the footpad with LL-2, Lewis lung carcinoma cells (1×10$^4$/mouse). The mice were maintained on a constant photoperiod for the duration of the treatment. Approximately 3 weeks following tumor cell injection when the primary tumor was 5–7 mm in diameter it was surgically removed and mice were divided into 7 groups (5–7 mice/group) and injected with prolactin (20 mcg/mouse) at 4, 8, 12, 16, or 20 hours after corticosterone (20 mcg/mouse) for 10 days. A control group remained untreated. After treatment was completed, the animals were placed on a 12 hour daily photoperiod with the dark period beginning 2 hours after the animals used to receive the corticosterone injection during the treatment period. Three days following the termination of treatment, mice were sacrificed to determine metastatic spread to the lung (determined by lung weight). The results are shown in Table 2.

TABLE 2

LUNG WEIGHT OF CONTROL MICE OR MICE INJECTED WITH LEWIS LUNG CARCINOMA CELLS

| time of PRL after corticosterone | no tumor control | tumor control | 0 hours | 4 hours | 8 hours | 12 hours | 16 hours | 20 hours |
|---|---|---|---|---|---|---|---|---|
| LUNG WEIGHT (mg) | 215 ± 10 | 404 ± 67 | 255 ± 28 | 255 ± 42 | 400 ± 74 | 328 ± 69 | 362 ± 60 | 360 ± 68 |

EXAMPLE 3

Effect of Timed Prolactin Injection on Tumor Growth in Balb/C Mice

Figure 4:
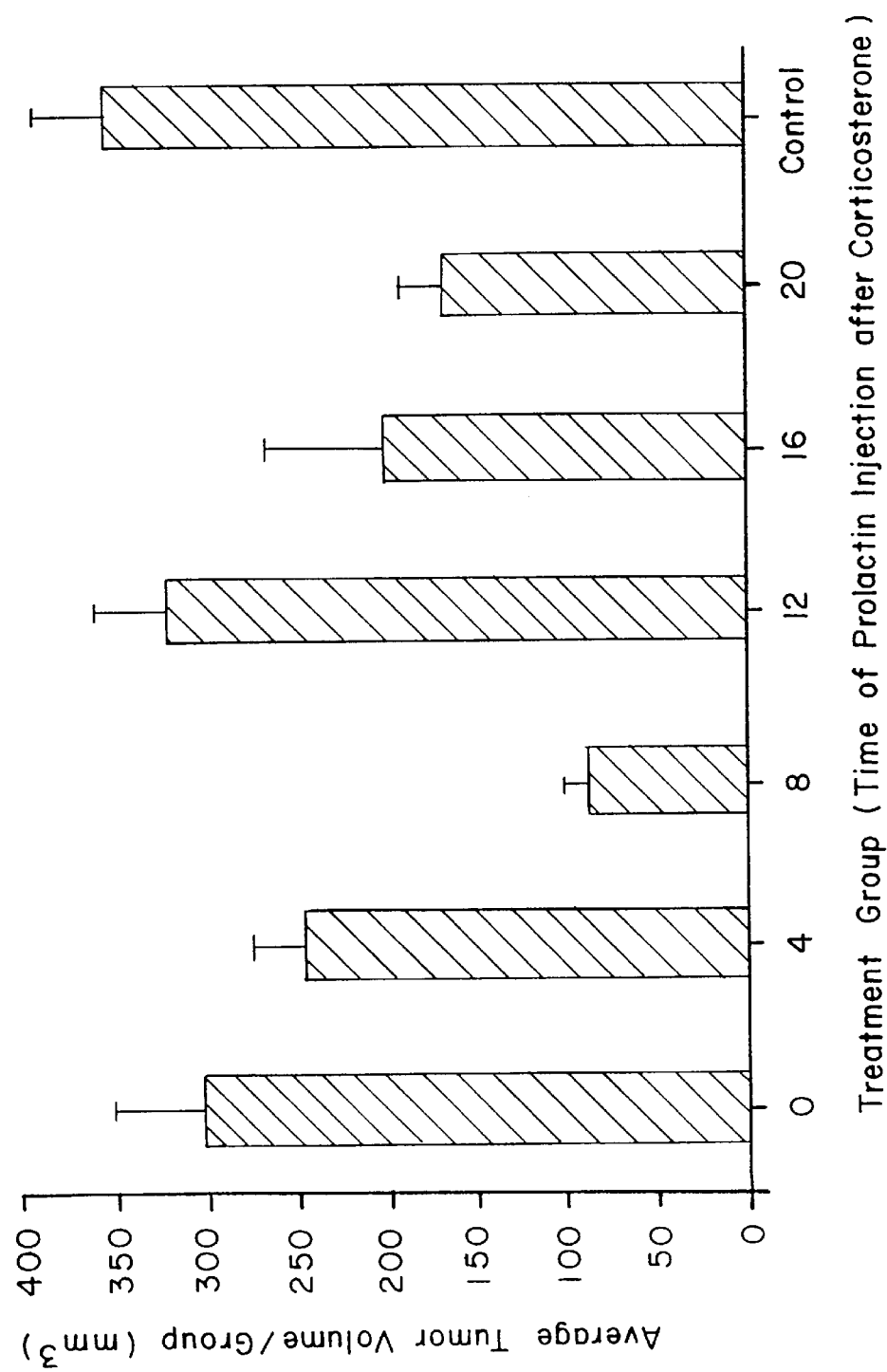
FIG. 4 is a bar graph illustrating the effect of timed prolactin injections on EMC-6 tumor growth in Balb/C mice whose circadian rhythms are being set by corticosterone injections.

Adult (6–7 week old) male Balb/C mice were transferred from 12 hour daily photoperiods to constant light for 10 days in order to disrupt circadian rhythms at which time EMT-6 tumor cells (1.7×10$^6$) were injected in the hind quarter. Following tumor cell inoculation mice were divided into 7 groups (10 mice/group) and injected daily for 10 days with ovine prolactin (20 mcg/mouse) at either 0, 4, 8, 12, 16, or 20 hours after corticosterone injection. A control group remained untreated. At the end of treatment animals were placed a 14 hour daily photoperiod with the dark period beginning 2 hours after the time the animals used to receive the corticosterone injection during the treatment period. Two weeks following the termination of treatment tumor volume was determined by caliper measurements. The results are shown in FIG. 4. Inhibition of tumor growth by prolactin treatment was found to be dependent on time of administration. It was determined that the greatest inhibition of tumor growth was in the 8 hour prolactin/corticosterone group (i.e., prolactin injected 8 hours after corticosterone injection) (85±15 mm$^3$ for 8 hour prolactin/corticosterone treated mice vs 350±35 mm$^3$ for untreated mice; P<0.01). This example demonstrates that tumor reduction is heavily dependent on the time of administration of prolactin relative to the induced corticosterone peak which, in the absence of a photoperiod, sets the circadian rhythms of the mice.

EXAMPLE 4

Effect of Timed Prolactin Injection on Metastatic Spread in Tumor Bearing Mice

Adult (6–7 week old) C57 Black male mice were transferred from 12 hour photoperiods to constant light for 7 days In healthy C57 Black mice on a constant photoperiod, prolactin secretion peaks at 0 hours after the peak corticosterone level. The results of this experiment show that maximum inhibition of tumor growth is achieved by injecting prolactin within 0–4 hours after the peak corticosterone level, i.e. at the same time that prolactin peaks after a corticosterone injection in healthy C57 Black mice on a constant photoperiod (a normal C57 Black prolactin profile).

Thus, timed injections of prolactin which occur at the same point in a circadian cycle that prolactin levels peak in healthy animals of the same species and sex can significantly decrease the degree of metastatic growth after a primary tumor is removed.

EXAMPLE 5

Figure 2:
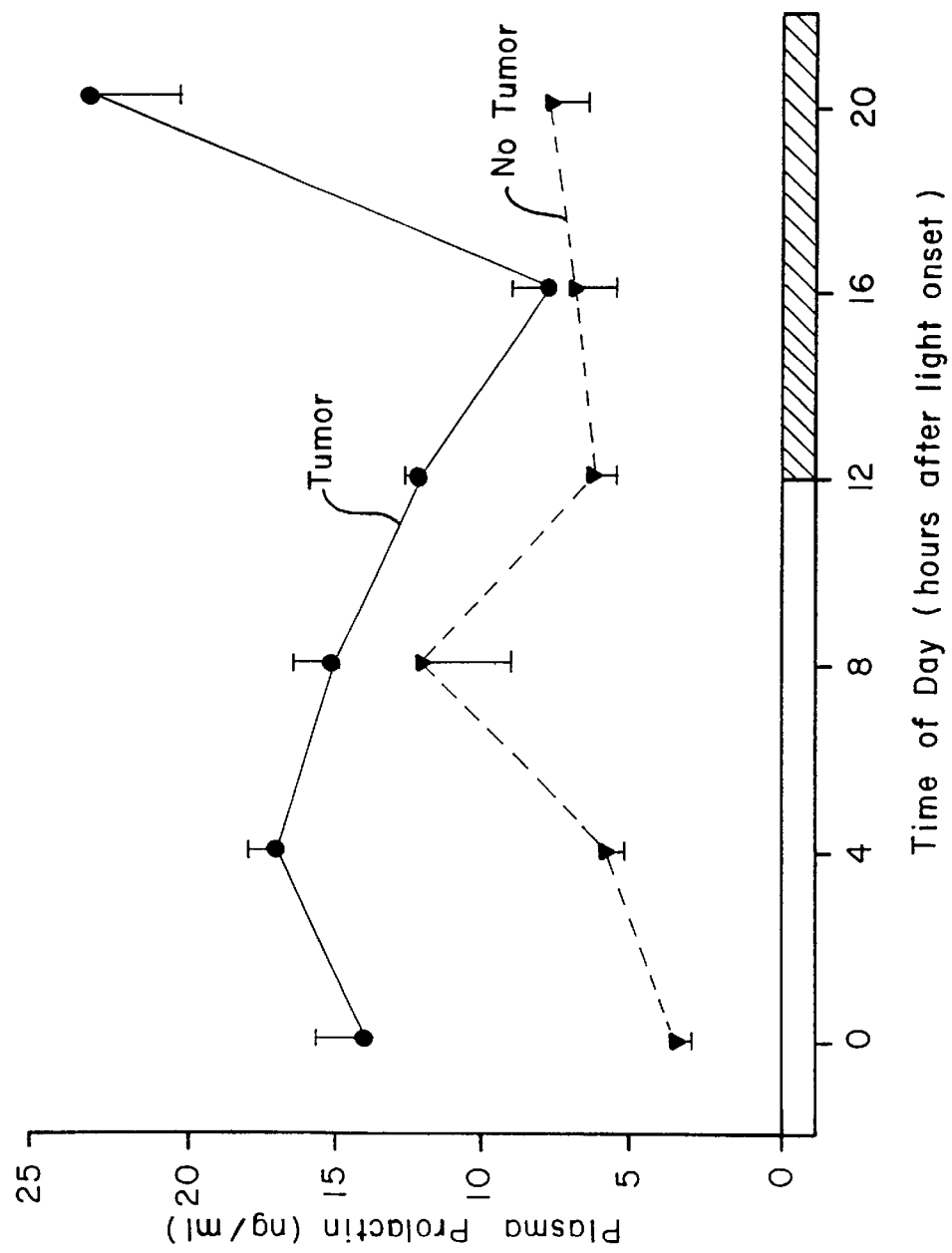
FIG. 2 is the prolactin daily rhythm or profile curve for mice with or without an implanted EMT-6 tumor.

Time Bromocriptine Administration Effect on Tumor Growth (EMT-6 Fibrosarcoma) in Balb/C Mice Adult (6–7 week old) male Balb/C mice on a 12 hour daily photoperiod are injected with EMT-6 tumor cells (1.7×10$^6$) in the hind quarter. Following tumor cell inoculation mice are divided into 7 groups (10 mice/group). Three groups are injected daily for 10 days with bromocriptine (50 mcg/mouse) at 0, 12 and 20 hours after light onset. Three groups (control) receive only a vehicle injection the same time (0, 12, and 20 HALO). A control group remains untreated. Two weeks following the termination of treatment tumor volume is determined by caliper measurements. Tumor growth will be inhibited by bromocriptine administration. Maximum inhibition of tumor growth by bromocriptine treatment will occur in those mice injected with bromocriptine at 0 hours after light onset. The maximum prolactin level occurs at 8–12 HALO. This corresponds to the prolactin profile of healthy Balb/C mice as shown in FIG. 2.

EXAMPLE 6

Timed Bromocriptine and Melatonin Administration Effect on Tumor Growth (EMT-6 Fibrosarcoma) in Balb/C Mice Adult (6–7 week old) male Balb/C mice are injected with EMT-6 tumor cells ($1.7 \times 10^6$) in the hind quarter. Following tumor cell inoculation mice are divided into 8 groups (10 mice/group) and are injected daily for 10 days with bromocriptine at 0 HALO, the time determined in Example 5 which results in the greatest inhibition of tumor growth (50 mcg/mouse). The mice are also injected with melatonin (40 mcg/mouse) at either 0, 4, 8, 12, 16, or 20 hours after bromocriptine injection. One control group remains untreated, and another control group is treated with only bromocriptine. Two weeks following the termination of treatment tumor volume is determined by caliper measurements. It is found that tumor growth is inhibited to a greater extent by the combination of timed bromocriptine at 0 HALO and melatonin administration at 12 hours after bromocriptine injection than by the timed administration of bromocriptine alone, and that the enhancement of inhibition of tumor growth by melatonin treatment is time of melatonin administration dependent. The maximum effect of melatonin is at 12 HALO because this stimulates prolactin release at the time of day that prolactin exhibits the greatest inhibitory activity against neoplastic growth and it is also the time of peak melatonin levels in healthy, non-metastasis bearing mice.

The method of the present invention can be used to treat a wide spectrum of neoplastic diseases including, by way of non-limiting example, sarcoma, fibrosarcoma, glioblastoma, carcinoma, melanoma, Hodgkin's and non-Hodgkin's lymphomas, leukemias, and other neoplastic conditions.

What is claimed is:

1. A method for treating a patient suffering from a neoplasm comprising the steps of:

comparing the blood prolactin level of said patient at each of a plurality of spaced apart time points during a 24-hour period to the corresponding prolactin level of a baseline prolactin profile for healthy humans of the same sex as said patient; and adjusting the prolactin level of said patient to cause the patient's prolactin profile to approach or conform to the baseline prolactin profile by administering a prolactin reducer to said mammal at a predetermined time, thereby inhibiting the growth of said neoplasm in said human.

2. The method of claim 1 wherein the prolactin level of said mammal is adjusted by administering to said mammal at a predetermined time a prolactin reducer when the daytime prolactin level of said mammal is higher than 1 SEM above the baseline prolactin profile at two spaced apart time points or when the daytime prolactin level of said mammal is higher than 2 SEM above the baseline prolactin profile at one time point.

3. The method of claim 2, wherein said prolactin reducer is bromocriptine.

4. The method of claim 3, wherein said neoplasm is selected from the group consisting of sarcomas, fibrosarcomas, carcinomas, glioblastomas, and melanomas.

5. The method of claim 3 wherein said bromocriptine is administered in an amount within the range of 0.8–8.0 mg/patient/day.

6. The method of claim 3 wherein said predetermined time is between 05:00 h and about 13:00 h.

7. The method of claim 6 wherein said predetermined time is between about 05:00 h and 10:30 h and said bromocriptine amount is within the range of 0.8–4.8 mg/patient/day.

8. The method of claim 1, wherein said prolactin reducer is bromocriptine.

9. The method of claim 8, wherein said bromocriptine is administered in an amount within the range of 0.8–8.0 mg/patient/day.

10. The method of claim 8, wherein said predetermined time is between 05:00 h and about 13:00 h.

11. The method of claim 8 wherein said neoplasm is selected from the group consisting of sarcomas, fibrosarcomas, carcinomas, glioblastomas, and melanomas.

12. The method of claim 1, further comprising administering a prolactin enhancer to said patient.

13. The method of claim 12, wherein said prolactin reducer is bromocriptine and said prolactin enhancer is melatonin.

14. The method of claim 13, wherein said neoplasm is selected from the group consisting of sarcomas, fibrosarcomas, carcinomas, glioblastomas, and melanomas.

15. The method of claim 2, which further comprises adjusting the prolactin profile of said patient by administering a prolactin enhancer to said patient when said patient's night time prolactin level is lower than 1 SEM below the baseline prolactin profile at two spaced apart time points or when said patient's night time prolactin level is lower than 2 SEM below the baseline prolactin profile at one time point.

16. The method of claim 15, wherein said prolactin reducer is bromocriptine and said prolactin enhancer is melatonin.

17. The method of claim 16, where said neoplasm is selected from the group consisting of sarcomas, fibrosarcomas, carcinomas, glioblastomas, and melanomas.

18. A method for treating a patient suffering from a neoplasm comprising adjusting the prolactin level of said patient to cause the patient's prolactin profile to approach or conform to the baseline prolactin profile by administering a prolactin reducer to said patient at a predetermined time, thereby inhibiting the growth of said neoplasm in said human.

19. The method of claim 18, wherein the prolactin level of said patient is adjusted by administering to said patient at a predetermined time a prolactin reducer when the daytime prolactin level of said patient is higher than 1 SEM above the baseline prolactin profile at two spaced apart time points or when the daytime prolactin level of said patient is higher than 2 SEM above the baseline prolactin profile at one time point.

20. The method of claim 18, wherein said prolactin reducer is bromocriptine.

21. The method of claim 20, wherein said bromocriptine is administered in an amount within the range of 0.8–8.0 mg/patient/day.

22. The method of claim 20, wherein said predetermined time is between 05:00 h and about 13:00 h.

23. The method of claim 20, wherein said neoplasm is selected from the group consisting of sarcomas, fibrosarcomas, carcinomas, glioblastomas, and melanomas.

24. The method of claim 19, wherein said prolactin reducer is bromocriptine.

25. The method of claim 24, wherein said bromocriptine is administered in an amount within the range of 0.8–8.0 mg/patient/day.

26. The method of claim 24, wherein said predetermined time is between about 5:00 h and about 13:00 h.

27. The method of claim 24, wherein said neoplasm is selected from the group consisting of sarcomas, fibrosarcomas, carcinomas, glioblastomas, and melanomas.

28. The method of claim 18, wherein said method further comprises administering a prolactin enhancer to said patient.

29. The method of claim 19, which further comprises adjusting the prolactin profile of said patient by administering a prolactin enhancer to said patient when said patient's night time prolactin level is lower than 1 SEM below the baseline prolactin profile at two spaced apart time points or when said patient's night time prolactin level is lower than 2 SEM below the baseline prolactin profile at one time point.

30. The method of claim 28, wherein said prolactin reducer is bromocriptine and said prolactin enhancer is melatonin.

31. The method of claim 30, where said neoplasm is selected from the group consisting of sarcomas, fibrosarcomas, carcinomas, glioblastomas, and melanomas.

32. The method of claim 29, wherein said prolactin reducer is bromocriptine and said prolactin enhancer is melatonin.

33. The method of claim 32, wherein said neoplasm is selected from the group consisting of sarcomas, fibrosarcomas, carcinomas, glioblastomas, and melanomas.

* * * * *